(12) United States Patent
Weber et al.

(10) Patent No.: US 9,546,177 B2
(45) Date of Patent: Jan. 17, 2017

(54) SYNTHESIS OF NOROXYMORPHONE FROM MORPHINE

(71) Applicant: SIEGFRIED AG, Zofingen (CH)

(72) Inventors: Beat Theodor Weber, Zofingen (CH); Lisa Hochstrasser, Trimbach (CH)

(73) Assignee: SIEGRIED AG, Zofingen (CH)

( * ) Notice: Subject to any disclaimer, the term of this patent is extended or adjusted under 35 U.S.C. 154(b) by 0 days.

(21) Appl. No.: 14/908,064

(22) PCT Filed: Jul. 22, 2014

(86) PCT No.: PCT/EP2014/065703
§ 371 (c)(1),
(2) Date: Jan. 27, 2016

(87) PCT Pub. No.: WO2015/011131
PCT Pub. Date: Jan. 29, 2015

(65) Prior Publication Data
US 2016/0159812 A1 Jun. 9, 2016

(30) Foreign Application Priority Data
Jul. 26, 2013 (EP) .................................... 13178119

(51) Int. Cl.
*C07D 489/08* (2006.01)
*C07D 489/02* (2006.01)

(52) U.S. Cl.
CPC ........... *C07D 489/02* (2013.01); *C07D 489/08* (2013.01)

(58) Field of Classification Search
USPC .................................................... 546/45, 44
See application file for complete search history.

(56) References Cited

U.S. PATENT DOCUMENTS

| | | | |
|---|---|---|---|
| 4,176,186 A | 11/1979 | Goldberg et al. | |
| 4,472,253 A | 9/1984 | Schwartz | |
| 4,795,813 A | 1/1989 | Schwartz | |
| 5,112,975 A * | 5/1992 | Wallace | C07D 489/08 546/44 |
| 5,869,669 A | 2/1999 | Huang et al. | |
| 5,922,876 A | 7/1999 | Huang et al. | |
| 5,948,788 A | 9/1999 | Huang et al. | |
| 5,952,495 A | 9/1999 | Huang et al. | |
| 6,008,354 A | 12/1999 | Huang et al. | |
| 6,008,355 A | 12/1999 | Huang et al. | |
| 6,013,796 A | 1/2000 | Huang et al. | |
| 8,921,557 B2 | 12/2014 | Weber et al. | |
| 2013/0035489 A1 | 2/2013 | Weber et al. | |

FOREIGN PATENT DOCUMENTS

| | | |
|---|---|---|
| EP | 0158476 A1 | 10/1985 |
| EP | 2377866 A1 | 10/2011 |
| FR | 2515184 A1 | 6/1987 |
| WO | 9902529 A1 | 1/1999 |

OTHER PUBLICATIONS

International Search Report for PCT/EP2014/065703 dated Sep. 30, 2014.
Swern, Pfitzner-Moffatt; Corey-Kim; S. Bayryamov, Conference Proceedings of the University of Ruse, vol. 49, 2010, pp. 9.1, Retrieved from the Internet <URL:http://conf.uni-ruse.bg/bg/docs/cp10/9.119.1-3.pdf>.
Omura, K.; Swern, D.: "Oxidation of alcohols by "activated" dimethyl sulfoxide. A preparative, steric and mechanistic study", Tetrahedron, vol. 34, No. 11, 1978, pp. 1651.
Ninan A.; Sainsbury M.: "An improved synthesis of noroxymorphone", Tetrahedron, vol. 48, No. 11, 1992, pp. 6709.

* cited by examiner

*Primary Examiner* — Charanjit Aulakh

(74) *Attorney, Agent, or Firm* — Millen, White, Zelano & Branigan, P.C.

(57) ABSTRACT

The present invention is directed to an improved process to convert morphine into noroxymorphone having economic and ecological advantages.

20 Claims, No Drawings

SYNTHESIS OF NOROXYMORPHONE FROM MORPHINE

The present invention is directed to a process to convert morphine into noroxymorphone having economic and ecological advantages.

FIELD OF THE INVENTION

Morphine and other naturally occurring opioids as well as their synthetically modified derivatives are compounds used as active pharmaceutical ingredients. Many of them show excellent activity in the human body. Hence, these substances are widely used in the treatment of e.g. pain, drug addiction problems, opioid induced constipation, intestinal immobilization and other diseases.

One key molecule in the synthesis of several synthetic opioid derived drug substances is noroxymorphone (compound I). The use of this substance as starting material for further syntheses has been demonstrated in U.S. Pat. No. 4,176,186. The present invention discloses an improved synthetic procedure for the manufacturing of noroxymorphone starting with a commonly available opioid: morphine (compound II).

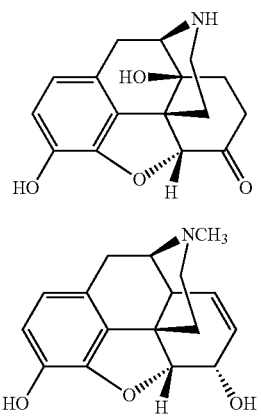

(I)

(II)

The process of producing noroxymorphone from morphine can in general be divided in six steps, wherein the following reactions are carried out:

Step (i): reacting morphine of formula (II) to a compound of formula (IIIa) or (IIIb), wherein $R^1$ and $R^{1'}$ independently are a substituted or unsubstituted alkyl group with 1 to 20 carbon atoms or a substituted or unsubstituted aryl group, preferably a substituted or unsubstituted alkyl group having 1 to 6 carbon atoms or a substituted or unsubstituted phenyl group, or a substituted or unsubstituted alkenyl group having 2 to 20 carbon atoms, preferably having 2 to 6 carbon atoms, or a substituted or unsubstituted carbonyloxyalkyl group with 1 to 20 carbon atoms in the alkyl residue or a substituted or unsubstituted carbonyloxyaryl group or a substituted or unsubstituted carbonyloxyalkylaryl group with 1 to 20 carbon atoms in the alkyl residue, preferably a substituted or unsubstituted carbonyloxyalkyl group having 1 to 6 carbon atoms in the alkyl residue or a substituted or unsubstituted carbonyloxyphenyl group, or a silyl group of formula $Si(R^4)_3$, wherein the groups $R^4$ can be the same or different and are each selected from substituted or unsubstituted alkyl groups having 1 to 6 carbon atoms and unsubstituted or substituted phenyl groups, e.g. as generally used in protecting group strategies as defined in the relevant literature (e.g. Peter G. M. Wuts, Theodora W. Greene: "Green's Protective Groups in Organic Synthesis", 4th Ed., John Wiley & Sons Inc., Hoboken, New Jersey), preferably wherein $R^1$ and $R^{1'}$ independently are a substituted or unsubstituted carbonyloxyalkyl group having 1 to 6 carbon atoms in the alkyl residue or a substituted or unsubstituted carbonyloxyphenyl group, respectively; i.e. $R^1$ and $R^{1'}$ preferably are independently a substituted or unsubstituted carbonyloxyalkyl group having 1 to 6 carbon atoms in the alkyl residue or a substituted or unsubstituted carbonyloxyphenyl group, respectively;

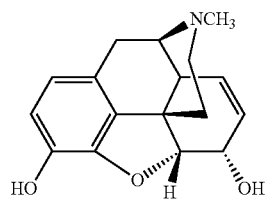

(II)

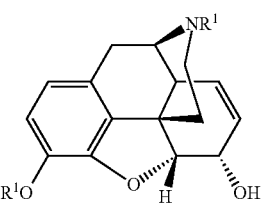

(IIIa)

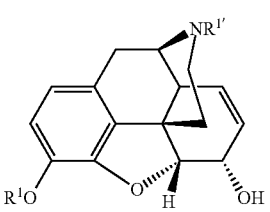

(IIIb)

Step (ii): reacting the compound of formula (IIIa) or (IIIb) to a compound of formula (IVa) or (IVb), respectively;

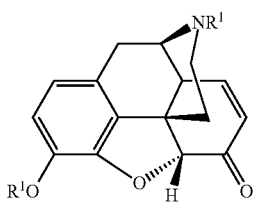

(IVa)

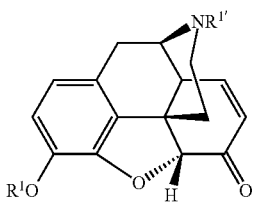

(IVb)

Step (iii): reacting the compound of formula (IVa) or (IVb) to a compound of formula (Va) or (Vb), respectively,

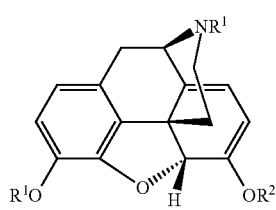
(Va)

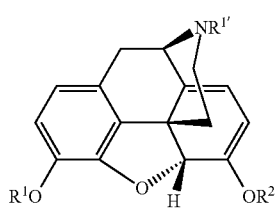
(Vb)

wherein $R^2$ is a substituted or unsubstituted aliphatic or aromatic acyl group with 1 to 20 carbon atoms, preferably a substituted or unsubstituted aliphatic acyl group with an alkyl residue having 1 to 6 carbon atoms or a substituted or unsubstituted benzoyl group, i.e. an acyl group with a phenyl residue on the carbon of the carbonyl;

Step (iv): reacting the compound of formula (Va) or (Vb) to a compound of formula (VIa) or (VIb), respectively;

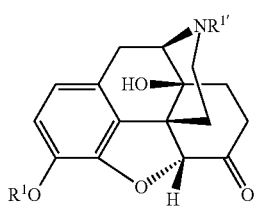
(VIa)

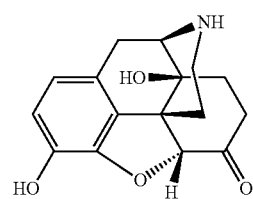
(VIb)

(v) reacting the compound of formula (VIa) or (VIb) to a compound of formula VIIa) or (VIIb), respectively; and

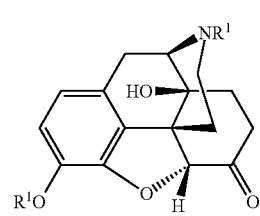
(VIIa)

(VIIb)

(vi) reacting the compound of formula (VIIa) or (VIIb) to noroxymorphone of formula (I), respectively.

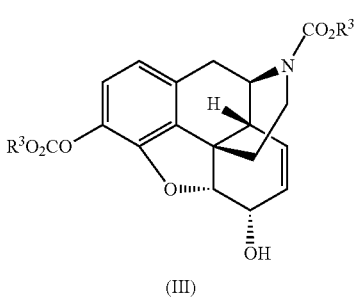
(I)

The respective process steps are generally known from the state of the art, which is exemplified in the following section.

BACKGROUND AND PRIOR ART

U.S. Pat. No. 5,112,975 (EP 0 158 476) discloses processes using morphine as starting material for manufacturing noroxymorphone. This 6-step process is illustrated in scheme 1.

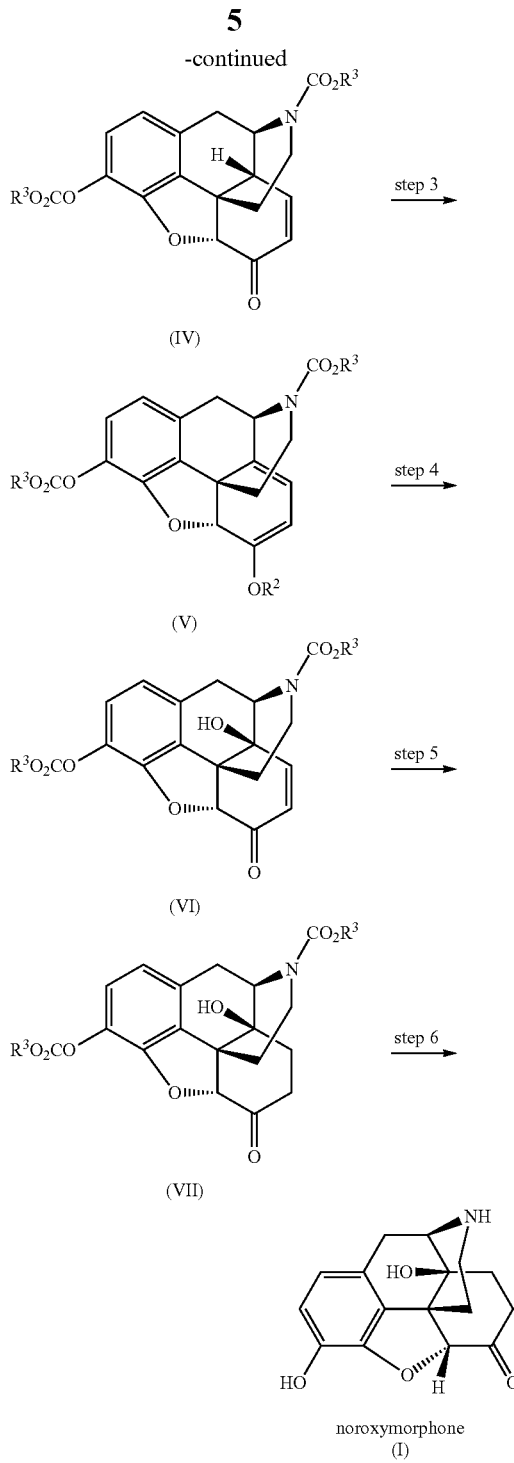

(IV)

(V)

(VI)

(VII)

noroxymorphone
(I)

Whereas the general outlay of the process looks attracting major drawbacks are noticed when reading the teachings as disclosed for the individual steps.

Step 1 is executed with the problematic solvent chloroform. According to the European Medicines Agency's Q3C (R4) Guideline for Residual Solvents chloroform is a highly problematic solvent that can only be tolerated in medical compositions in a maximal concentration of 60 ppm.

Step 2 is executed with Jones' reagent, a Cr(VI) reagent bearing an inherent risk for both product safety and environment. An alternate methodology is disclosed by Schwartz in FR 2 515 184 (U.S. Pat. No. 4,795,813). N-ethoxycarbonylnorcodeine (compound III) may be oxidized by manganese dioxide. However, oxidations with manganese dioxide are very sensitive to the nature of the reagent, which widely varies for commercially available material. Typically a huge excess of manganese dioxide is needed (Ninan A.; Sainsbury M. (1992). "An improved synthesis of noroxymorphone", Tetrahedron 48 (11): 6709) making this process costly and generating significant amounts of wastes.

For step 4 FR 2 515 184 discloses that peracids may be used for this transformation. The peracids may be either formed in situ by mixing hydrogen peroxide with acids or acid anhydrides or be used as isolated compounds. Isolated peracids are hazardous compounds due to their intrinsic nature to decompose. Therefore handling and storing these compounds is demanding. In situ generated peracids overcome the storage and transport problems however, reported yields for simple organic acids such as acetic and formic acids are low (38% and 33%, respectively). Maleic acid would allow higher yields; however, additional solvents are needed.

For step 6 FR 2 515 184 reports as being performed with moderate yield only. The di-ethoxycarbonyl compound yields 60% noroxymorphone only. This may be due to the harsh reaction conditions needed for the hydrolysis of the ethoxycarbonyl amide moiety. More gentle conditions can be used if alternate oxycarbonyl amide compounds are used. However, viable substitutes such as alpha-chloroethoxycarbonyl amide are significantly more expensive see for example Peter G. M. Wuts, Theodora W. Greene: "Green's Protective Groups in Organic Synthesis", 4th Ed., John Wiley & Sons Inc., Hoboken, N.J.).

The reported overall yield in FR 2 515 184 for the 6 step synthesis does not exceed 37%.

The overall yield of 37% for reactions of the state of the art is asking for further investigations to improve ecological and economic aspects of the process and to reduce the use of toxic agents and solvents.

Hence, there is still a need for an improved process for producing noroxymorphone from morphine.

SUMMARY OF THE INVENTION

The current invention presents an improved process which addresses the issues as discussed above. The present invention relates to an improved process for producing noroxymorphone from morphine wherein a remarkable improvement in the process can be achieved in the step of reacting a compound of formula (Va) or (Vb), wherein $R^1$ and $R^{1'}$ independently are a substituted or unsubstituted alkyl group with 1 to 20 carbon atoms or a substituted or unsubstituted aryl group, preferably a substituted or unsubstituted alkyl group having 1 to 6 carbon atoms or a substituted or unsubstituted phenyl group, or a substituted or unsubstituted alkenyl group having 2 to 20 carbon atoms, preferably having 2 to 6 carbon atoms, or a substituted or unsubstituted carbonyloxyalkyl group with 1 to 20 carbon atoms in the alkyl residue, or a substituted or unsubstituted carbonyloxyaryl group or a substituted or unsubstituted carbonyloxyalkylaryl group with 1 to 20 carbon atoms in the alkyl residue, preferably a substituted or unsubstituted carbonlyoxyalkyl group having 1 to 6 carbon atoms in the alkyl residue or a substituted or unsubstituted carbonyloxyphenyl group, or a silylgroup of formula $Si(R^4)_3$, wherein the groups $R^4$ can be the same or different and are each selected from substituted or unsubstituted alkyl groups having 1 to 6 carbon atoms and unsubstituted or substituted phenyl groups, e.g. as generally used in protecting group strategies as defined in the relevant literature (e.g. Peter G. M. Wuts, Theodora W. Greene: "Green's Protective Groups in Organic Synthesis", 4th Ed., John Wiley & Sons Inc., Hoboken, N.J.), respectively, preferably wherein $R^1$ and $R^{1'}$ independently are a substituted or unsubstituted carbonyloxyalkyl group having 1 to 6 carbon atoms in the alkyl residue or a substituted or unsubstituted carbonyloxyphenyl group, respectively, and wherein $R^2$ is a substituted or unsubstituted aliphatic or aromatic acyl group with 1 to 20 carbon atoms, preferably a substituted or unsubstituted aliphatic acyl group with an alkyl residue having 1 to 6 carbon atoms or a substituted or unsubstituted benzoyl group;

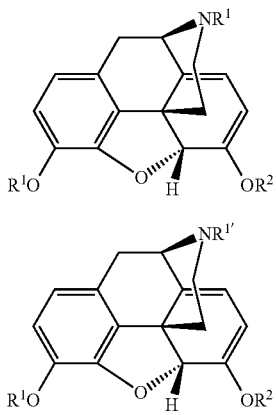

(Va)

(Vb)

to a compound of formula (VIa) or (VIb), respectively.

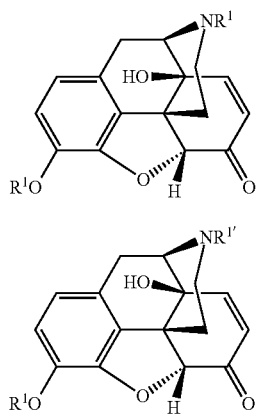

(VIa)

(VIb)

In the formulas $R^1$ and $R^{1'}$ preferably are independently a substituted or unsubstituted carbonyloxyalkyl group having 1 to 6 carbon atoms in the alkyl residue or a substituted or unsubstituted carbonyloxyphenyl group, respectively.

In one aspect the present invention relates to a process for producing noroxymorphone from morphine wherein morphine is reacted to a compound of formula (Va) or (Vb), wherein $R^1$ and $R^{1'}$ independently are a substituted or unsubstituted alkyl group with 1 to 20 carbon atoms or a substituted or unsubstituted aryl group, preferably a substituted or unsubstituted alkyl group having 1 to 6 carbon atoms or a substituted or unsubstituted phenyl group, or a substituted or unsubstituted alkenyl group having 2 to 20 carbon atoms, preferably having 2 to 6 carbon atoms, or a substituted or unsubstituted carbonyloxyalkyl group with 1 to 20 carbon atoms in the alkyl residue, or a substituted or unsubstituted carbonyloxyaryl group or a substituted or unsubstituted carbonyloxyalkylaryl group with 1 to 20 carbon atoms in the alkyl residue, preferably a substituted or unsubstituted carbonlyoxyalkyl group having 1 to 6 carbon atoms in the alkyl residue or a substituted or unsubstituted carbonyloxyphenyl group, or a silylgroup of formula $Si(R^4)_3$, wherein the groups $R^4$ can be the same or different and are each selected from substituted or unsubstituted alkyl groups having 1 to 6 carbon atoms and unsubstituted or substituted phenyl groups, e.g. as generally used in protecting group strategies as defined in the relevant literature (e.g. Peter G. M. Wuts, Theodora W. Greene: "Green's Protective Groups in Organic Synthesis", 4th Ed., John Wiley & Sons Inc., Hoboken, N.J.), respectively, preferably wherein $R^1$ and $R^{1'}$ independently are a substituted or unsubstituted carbonyloxyalkyl group having 1 to 6 carbon atoms in the alkyl residue or a substituted or unsubstituted carbonyloxyphenyl group, respectively, and wherein $R^2$ is a substituted or unsubstituted aliphatic or aromatic acyl group with 1 to 20 carbon atoms, preferably a substituted or unsubstituted aliphatic acyl group with an alkyl residue having 1 to 6 carbon atoms or a substituted or unsubstituted benzoyl group,

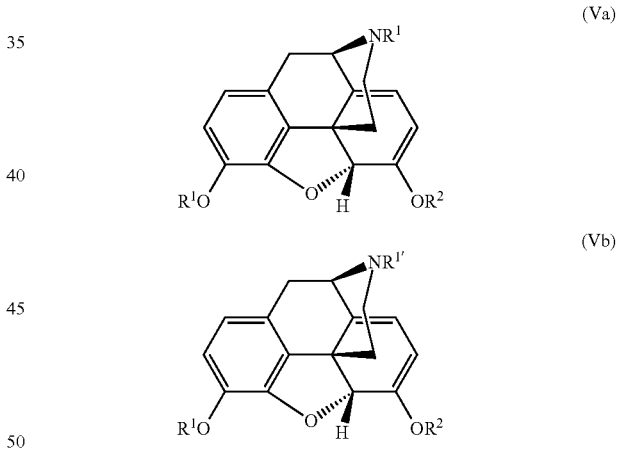

wherein the compound of formula (Va) or (Vb) is reacted to a compound of formula (VIa) or (VIb), respectively, and the compound of formula (VIa) or (VIb) is then reacted to noroxymorphone

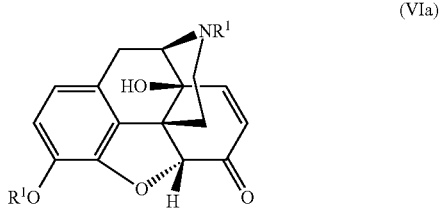

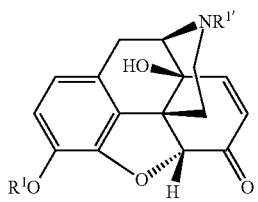
(VIb)

characterized in that the reaction of the compound of formula (Va) or (Vb) to the compound of formula (VIa) or (VIb) is carried out with hydrogen peroxide and an organic acid, wherein the organic acid and the hydrogen peroxide are mixed and allowed to react for a defined induction time prior to addition to the compound of formula (V).

In the above residues $R^1$, $R^{1'}$, $R^2$ and $R^4$ suitable substituents can be selected from halogen like fluoride, chloride, bromide and iodide or alkoxy residues with 1 to 6 carbon atoms, and a suitable substituent is thus also e.g. a chloroethyl or halogenated or alkoxylated phenyl residue or a carbonyloxychloroethyl or halogenated or alkoxylated carbonyloxyphenyl residue in the case of $R^1$ and $R^{1'}$ or a halogenated or alkoxylated benzoyl residue in the case of $R^2$.

In another aspect, the present invention is directed to process for reacting a compound of formula (Va) or (Vb) to a compound of formula (VIa) or (VIb), wherein $R^1$ and $R^{1'}$ independently are a substituted or unsubstituted alkyl group with 1 to 20 carbon atoms or a substituted or unsubstituted aryl group, preferably a substituted or unsubstituted alkyl group having 1 to 6 carbon atoms or a substituted or unsubstituted phenyl group, or a substituted or unsubstituted alkenyl group having 2 to 20 carbon atoms, preferably having 2 to 6 carbon atoms, or a substituted or unsubstituted carbonyloxyalkyl group with 1 to 20 carbon atoms in the alkyl residue, or a substituted or unsubstituted carbonyloxyaryl group or a substituted or unsubstituted carbonyloxyalkylaryl group with 1 to 20 carbon atoms in the alkyl residue, preferably a substituted or unsubstituted carbonlyoxyalkyl group having 1 to 6 carbon atoms in the alkyl residue or a substituted or unsubstituted carbonyloxyphenyl group, or a silylgroup of formula $Si(R^4)_3$, wherein the groups $R^4$ can be the same or different and are each selected from substituted or unsubstituted alkyl groups having 1 to 6 carbon atoms and unsubstituted or substituted phenyl groups, e.g. as generally used in protecting group strategies as defined in the relevant literature (e.g. Peter G. M. Wuts, Theodora W. Greene: "Green's Protective Groups in Organic Synthesis", 4th Ed., John Wiley & Sons Inc., Hoboken, N.J.), respectively, preferably wherein $R^1$ and $R^{1'}$ independently are a substituted or unsubstituted carbonyloxyalkyl group having 1 to 6 carbon atoms in the alkyl residue or a substituted or unsubstituted carbonyloxyphenyl group, respectively, and wherein $R^2$ is a substituted or unsubstituted aliphatic or aromatic acyl group with 1 to 20 carbon atoms, preferably a substituted or unsubstituted aliphatic acyl group with an alkyl residue having 1 to 6 carbon atoms or a substituted or unsubstituted benzoyl group, characterized in that the reaction is carried out with hydrogen peroxide and an organic acid, wherein the organic acid and the hydrogen peroxide are mixed and allowed to react for a certain induction time prior to addition to the compound of formula (Va) or (Vb).

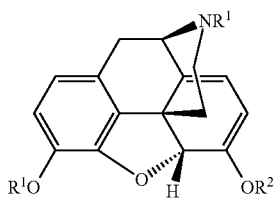
(Va)

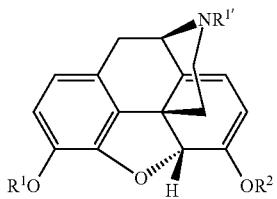
(Vb)

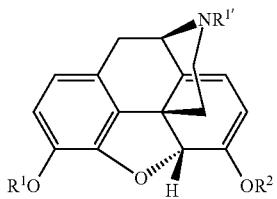
(VIa)

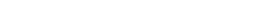
(VIb)

Further preferred embodiments of the present invention are defined in the dependent claims.

DETAILED DESCRIPTION OF THE INVENTION

In the following the present invention will be explained in detail with reference to certain embodiments and examples thereof; however, the invention is not limited to these embodiments and examples.

Definitions:

In the present invention an organic acid is an acid of an organic compound, i.e. a compound that contains carbon atoms. Preferred among the organic acids, unless stated specifically otherwise, are carboxylic acids and sulfonic acids, and more preferred are carboxylic acids. In particular carboxylic acids with 1 to 6 carbon atoms are preferred, e.g. formic acid, acetic acid, propionic acid, and particularly preferred are formic acid and acetic acid, especially formic acid.

In the residues $R^1$, $R^{1'}$, $R^2$, $R^3$ and $R^4$ the alkyl and alkenyl structures in the different residues can be linear or branched.

Suitable substituents in the groups $R^1$, $R^{1'}$, $R^2$, $R^3$ and $R^4$ can be independently and suitably selected by the skilled person. Suitable substituents include for example halogen groups like fluoride, chloride, bromide and iodide, or alkoxy residues with 1 to 6 carbon atoms, and a suitable group is thus also e.g. a chloroethyl or halogenated or alkoxylated phenyl residue or a carbonyloxychloroethyl or halogenated or alkoxylated carbonyloxyphenyl residue in the case of $R^1$ and $R^{1'}$ or a halogenated or alkoxylated benzoyl residue in the case of $R^2$. For the compounds of formulas (III), (IIIa) and (IIIb), (IV), (IVa) and (IVb), (V), (Va) and (Vb), (VI), (VIa) and (VIb), (VII), (VIIa) and (VIIb) and (VIII), (VIIIa) and (VIIIb) preferred compounds are those wherein the residues $R^1$, $R^{1'}$, $R^2$, $R^3$ and $R^4$ are selected each from the preferred residues, respectively.

In the different compounds disclosed the groups $R^1$, $R^{1'}$, $R^2$, and $R^4$, can be the same or different in each compound as long as they do not change in a reaction step where they are present before and after the reaction. It is also possible that only $R^1$ and $R^{1'}$ are the same or different and $R^2$ is different from both $R^1$ and $R^{1'}$.

Among the compounds in the present process, the compound of formula (IIIa) is preferred among the compounds of formula (IIIa) and (IIIb), the compound of formula (IVa) is preferred among the compounds of formula (IVa) and (IVb), the compound of formula (Va) is preferred among the compounds of formula (Va) and (Vb), the compound of formula (VIa) is preferred among the compounds of formula (VIa) and (VIb), and the compound of formula (VIIa) is preferred among the compounds of formula (VIIa) and (VIIb). Thus among the compounds it is preferred that the residue $R^{1'}$ is equal to $R^1$. A preferred reaction thus proceeds from the compound of formula (II) in step (i) to a compound of formula (IIIa), then to a compound of formula (IVa) in step (ii), then to a compound of formula (Va) in step (iii), then to a compound of formula (VIa) in step (iv), then to a compound of formula (VIIa) in step (v), and finally to hydroxymorphinone, the compound of formula (I), in step (vi).

In certain aspects, a further preferred compound of formula (IIIa) or (IIIb), in particular (IIIa), is a compound of formula (III),

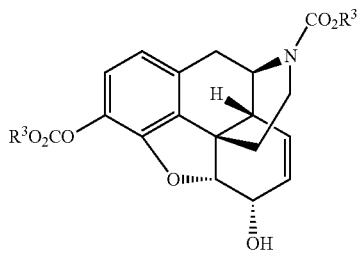

a further preferred compound of formula (IVa) or (IVb), in particular (IVa), is a compound of formula (IV),

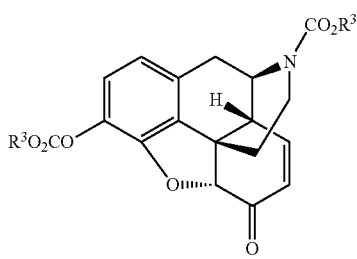

a further preferred compound of formula (Va) or (Vb), in particular (Va), is a compound of formula (V),

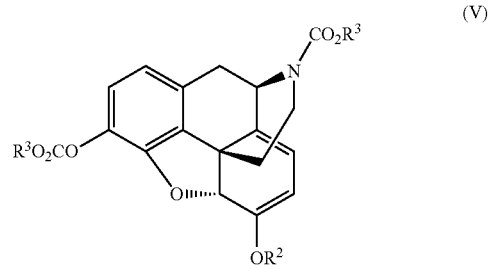

a further preferred compound of formula (VIa) or (VIb), in particular (VIa), is a compound of formula (VI),

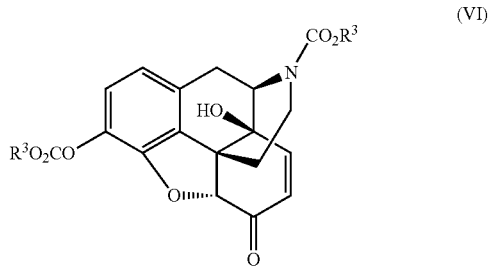

and a further preferred compound of formula (VIIa) or (VIIb), in particular (VIIa), is a compound of formula (VII), wherein $R^3$ in the compounds of formulas (III) to (VII) is a substituted or unsubstituted alkyl group with 1 to 20 carbon atoms or a substituted or unsubstituted aryl group, preferably a substituted or unsubstituted alkyl group having 1 to 6 carbon atoms or a substituted or unsubstituted phenyl group, and $R^2$ in formula (V) is as defined above for formulas (Va) and (Vb). Suitable substituents in $R^2$ and $R^3$ are as defined above for groups $R^1$, $R^{1'}$, $R^2$ and $R^4$.

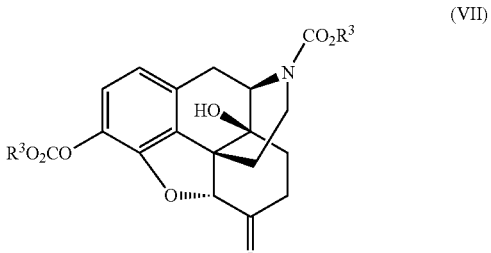

A further preferred reaction thus proceeds from the compound of formula (II) in step (i) to a compound of formula (III), then to a compound of formula (IV) in step (ii), then to a compound of formula (V) in step (iii), then to a compound of formula (VI) in step (iv), then to a compound of formula (VII) in step (v), and finally to hydroxymorphinone, the compound of formula (I), in step (vi).

In certain embodiments, the invention thus relates to the issues discussed for step 1 and/or step 2 and/or, step 4 and/or the de-protection issue at step 6 noted in the above state of the art FR 2 515 184.

In a preferred embodiment thus also a process for reacting a compound of formula (V) to a compound of formula (VI) is disclosed wherein $R^3$ and $R^2$ are as defined above, characterized in that the reaction is carried out with hydrogen peroxide and an organic acid, wherein the organic acid and the hydrogen peroxide are mixed and allowed to react for a certain induction time prior to addition to the compound of formula (V).

In certain embodiments of the invention the mixing and reacting of the hydrogen peroxide and the organic acid in step (iv) is carried out in a separate vessel. In some embodiments the compound of formula (Va) or (Vb), or of formula (V), respectively, is present in one vessel, whereas the hydrogen peroxide and the organic acid are mixed in another, separate vessel, and after a defined induction time the reacted mixture of hydrogen peroxide and organic acid is added to the vessel with the compound of formula (Va) or (Vb), or formula (V), respectively. The type of addition is not particularly limited and can be done in bulk or added in a controlled manner over a certain time. It is preferred to add the reacted mixture in a controlled manner over a certain period of time to ensure that a more homogeneous mixing can be achieved, and to minimize concentration gradients. To further minimize gradients it is also possible in certain embodiments to stir the vessel wherein the compound of formula (Va) or (Vb), or formula (V), respectively, optionally in a suitable solvent, is contained. It is also possible that the compound of formula (Va) or (Vb), or formula (V), respectively, is also flown continuously, optionally in a solvent, while adding the reacted mixture of hydrogen peroxide and organic acid. The mixing and reacting of the hydrogen peroxide and the organic acid can in certain embodiments be carried out by dosing two flows via a mixer, e.g. one of hydrogen peroxide and one of organic acid, preferably in a continuous flow device. Of course it can also be contemplated to add the compound of formula (Va) or (Vb), or formula (V), respectively, continuously in a controlled manner to a reacted mixture of hydrogen peroxide and organic acid. Suitable mixing methods of the compound of formula (Va) or (Vb), or formula (V), respectively, and the reacted mixture of hydrogen peroxide and organic acid are known to the skilled person.

Formic acid or acetic acid are preferably used as organic acid in step (iv), and preferably formic acid is used.

In certain embodiments the induction time between the hydrogen peroxide and the organic acid is between 1 minute and 1 hour, preferably between 10 and 30 minutes and further preferably between 10 and 20 minutes. When the induction time is too short the reaction cannot be improved sufficiently, whereas a too long induction time does not change the reaction any more. The mixing and reacting of hydrogen peroxide and the organic acid can further be carried out at a temperature between −20° C. and 40° C., preferably room temperature. It is further preferred that the addition of the reacted mixture of hydrogen peroxide and the organic acid to the compound of formula (Va) or (Vb), respectively the compound of formula (V), is carried out over a time from 1 minute to 3 hours, preferably over a time from 1 to 2.5 hours and further preferably over a time from 1 to 2 hours at a temperature between −40° C. and 40° C., preferably −20° C. and 20° C., further preferably about 0° C., e.g. in case of a stirred reactor.

The mixing ratio between hydrogen peroxide and the organic acid can be suitably set by the skilled person based on his general knowledge and can e.g. be set in a range from 20:1 to 1:20, preferably 1:1 to 1:10.

It can be preferred in step (iv) that a part of the organic acid is added to the compound of formula (Va) or (Vb), or the compound of formula (V), respectively, prior to the addition of the mixture of hydrogen peroxide and the remaining organic acid. Thereby the amount of organic acid can be reduced, thus leading to a more ecological and economical process, and which in particular can lead to a better recycling of the residual acid in case the acid is used as solvent and which can also avoid waste acid. Further, the reaction can also be enhanced by adding part of the organic acid due to better solubility of the compound of formula (Va) or (Vb), or the compound of formula (V), respectively.

In certain embodiments furthermore an aging step (iv-a) can be carried out after the reaction of the compound of formula (Va) or (Vb), or the compound of formula (V), respectively to the compound of formula (VIa) or (VIb), or the compound of formula (VI), respectively, for 1 to 5 hours at a temperature between −40° C. and 40° C., preferably −20° C. and 20° C., further preferably about 0° C., and the obtained mixture can be optionally worked up afterwards.

A suitable work-up of the mixture is known to the skilled person and can comprise e.g. a further cleaning, recrystallization, filtration, etc.

According to certain embodiments step (i) is carried out in absence of a highly toxic solvent. In certain embodiments of the present process step (i) can be carried out in absence of chloroform. According to the European Medicines Agency's Q3C (R4) Guideline for Residual Solvents chloroform is a highly problematic solvent that can only be tolerated in medical compositions in a maximal concentration of 60 ppm. The absence of chloroform enables a reduction of cost of the whole process as it does not need the reported high reaction temperature of boiling chloroform (61° C.) or a prolonged reaction time as predicted by the Arrhenius equation. Instead of chloroform, a less problematic solvent like dichloromethane, whose maximal concentration according to the European Medicines Agency's Q3C (R4) Guideline for Residual Solvents (http://www.ema.europa.eu/docs/en_GB/document_library/Scientific_guideline/2009/09/WC500002674.pdf) is 600 ppm, can be used. A highly toxic solvent according to the invention is a solvent which has a maximum concentration according to the European Medicines Agency's Q3C (R5) Guideline for Residual Solvents in a pharmaceutical product of less than 500 ppm, preferably less than 300 ppm and particularly preferably less than 100 ppm. Examples of highly toxic solvents include benzene, chloroform, methylbutylketone, 2-methoxyethanol, cumene, 1,2-dimethoxyethane, chlorobenzene, acetonitrile, 1,4-dioxane, 2-ethoxethanol, formamide, hexane, N-methylpyrrolidone, nitromethane, pyridine, sulfolane, tetraline, and 1,1,2-trichlorethane. The reaction can e.g. be performed at reflux temperature of dichloromethane (40° C.) using a base, e.g. a solid base like potassium hydrogen carbonate. The absence of chloroform enables an ecological and economically advantageous process as no chloroform is present in the final product and furthermore a costly separation of chloroform from the product can be avoided.

In further certain embodiments, step (ii) is conducted using a Swern oxidation with pre-cooled solutions. The Swern reaction (Omura, K.; Swern, D. (1978). "Oxidation of alcohols by "activated" dimethyl sulfoxide. A preparative, steric and mechanistic study", Tetrahedron 34 (11): 1651) is known since decades and the application of this reaction in the field of opiates is reported already. For example in U.S. Pat. No. 5,952,495 the Swern oxidation of several morphine derivatives is reported. However, none of the previous reports discloses a conversion of a compound of formula (IIIa) or (IIIb), or a compound of formula (III), respectively, into a compound of formula (IVa) or (IVb), or a compound of formula (IV), respectively.

In the Swern oxidation, as understood within the scope of this invention, generally a primary or secondary alcohol is oxidized under mild conditions to an aldehyde or ketone using dimethylsulfoxide (DMSO), an acid halide or acid anhydride like oxalylchloride and a base, e.g. organic bases like tertiary amines, for example triethylamine and diisopropylethylamine, or inorganic bases like an aqueous NaOH solution. Preferably the Swern oxidation is carried out using DMSO, oxalylchloride and a tertiary amine as base, i.e. classical Swern reactants. Alternately to the Swern conditions other combinations of a sulfoxide e.g. DMSO and activating reagents such as N,N'-dicyclohexylcarbodiimide (Pfitzner-Moffatt reaction), a pyrdine x SO₃ complex (Parikh-Doering reaction), or TBTU (o-(Benzotriazol-1-yl)-N,N,N',N'-tetramethyluronium tetrafluoroborate) (see "A new mild and selective method for oxidation of primary and secondary alcohols and amines, as well as amino acids, using a modification of Swern, Pfitzner-Moffatt and Corey-Kim", S. Bayryamov, Conference Proceedings of the University of Ruse, 2010, 49, 9.1; http://conf.uni-ruse.bg/bg/docs/cp10/9.1/9.1-3.pdf) may be used. Preferably classical Swern conditions are used due to the low reagent costs applied in the Swern reaction.

The reactants in the Swern oxidation can be each provided as solutions as necessary, and the skilled person knows how to prepare such solutions of the reactants. The skilled person in general also knows the molar ratios of the compounds used in the reaction in step (ii) and can set the amount of each reactant accordingly.

In the present process, the DMSO is generally first reacted with the acid halide or acid anhydride, like oxalylchloride, forming a sulfonium ion, and then the compound of formula (IIIa) or (IIIb), or the compound of formula (III), respectively, is added to the reaction mixture. After the reaction of the sulfonium ion with the compound of formula (IIIa) or (IIIb), or the compound of formula (III), respectively, the base is added for deprotonation and formation of the compound of formula (IVa) or (IVb), or the compound of formula (IV), respectively. The addition of the reactants is thereby preferably carried out under pre-cooled conditions, i.e. preferably all of the reagents are cooled during the addition below the ambient temperature, which can be between 15 and 30° C.

In the Swern oxidation according to the present invention, pre-cooled conditions can encompass e.g. precooling of the solutions added in step (ii) and/or adding of the solutions either via a cold reactor wall or via a separate cooling device. In certain embodiments the pre-cooled solutions in step (ii) are cooled to a temperature between −100° C. and 0° C., preferably −90° C. and −20° C. and/or are added either via a cold reactor wall or via a separate cooling device that are cooled to a temperature between −100° C. and 0° C., preferably cooled to a temperature between −90° C. and −20° C. In preferred embodiments the pre-cooled solutions in step (ii) are cooled to a temperature between −100° C. and 0° C., preferably −90° C. and −20° C. and are added either via a cold reactor wall or via a separate cooling device that are cooled to a temperature between −100° C. and 0° C., preferably cooled to a temperature between −90° C. and −20° C.

When the reported protocol for a Swern oxidation from U.S. Pat. No. 5,952,495 is applied surprisingly significant amounts of an un-described by-product are formed when using the compound of formula (IIIa) or (IIIb), or the compound of formula (III), respectively. Hence, a significant yield reduction is associated with the formation of this by-product. Analysis of the by-product reveals that the compound is an addition product of the compound of formula (IVa) or (IVb), or the compound of formula (IV), respectively, and methylsulfide. The structure of the by-product is shown as formula (VIIIa) or (VIIIb), or formula (VIII), respectively. It has been found that the formation of the compound of formula (VIIIa) or (VIIIb), or formula (VIII), respectively, can be suppressed if the addition of the solutions are added in the manner according to step (ii) of the invention with pre-cooled solution, i.e. if the Swern oxidation is done in such a manner that cold solutions are dosed onto the respective reaction mixture. This can be done for example if the solutions are dosed via the cold reactor wall or via a separate cooling device, and/or if the solutions are pre-cooled separately.

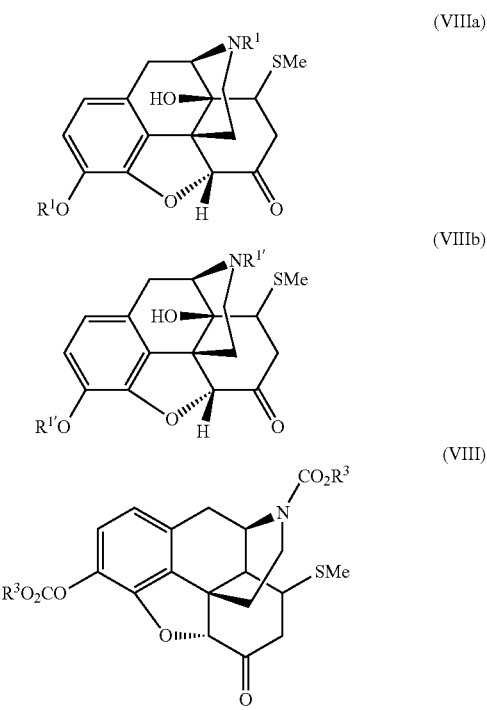

Furthermore, in certain embodiments, step (vi) is carried out in the presence of an organic solvent. Step (vi) can be carried out with a mixture comprising an aqueous acid and an organic solvent miscible with the aqueous acid, preferably wherein the organic solvent miscible with the aqueous acid is selected from the group consisting of alcohols, ethers, polyethers, sulfones and sulfoxides, or with a mixture comprising an aqueous organic acid. In step (vi) the skilled person thereby can suitably set the amounts of the reagents used as well as the reaction temperature and time.

The reaction of the compound of formula (VIIa) or (VIIb), or the compound of formula (VII), respectively, to noroxymorphone can be preferably carried out in a mixture of an organic solvent and an aqueous acid. The properties of the organic solvent shall allow mixing with the aqueous acid and show some solubility improvement to the compound of formula (VIIa) or (VIIb), or the compound of formula (VII), respectively.

Solvents that have these properties are for example alcohols, polyethers, and sulfoxides. The addition of the solvent to the saponification mixture surprisingly results in a significantly higher yield of noroxymorphone.

In step (vi) it is preferred to use a mixture of an aqueous acid and an alcohol. The use of alcohol allows a reduction of the amount of acid necessary in step (vi), which can save energy and time as well as reactants in a further work-up of the produced noroxymorphone, e.g. during a neutralization with a base for obtaining noroxymorphone.

An aqueous acid is thereby a mixture of water and an acid, and the acid can thereby be an organic acid or an inorganic acid. Suitable organic acids include methane sulfonic acid, p-toluene sulfonic acid, trichloroacetic acid, glacial acetic acid, and suitable inorganic acids are e.g. sulfuric acid, hydrochloric acid, hydrobromic acid. Also mixtures of two or more organic and/or inorganic acids can be used, e.g. mixtures of hydrochloric or hydrobromic acid with glacial acetic acid, or mixtures of formic acid with sulfuric acid, hydrochloric acid, etc. Preferably used is sulfuric acid from an ecological an economical viewpoint.

Suitable alcohols in step (vi) are alcohols with1 to 20 carbon atoms, and among these alcohols with 1 to 6 carbon atoms are preferable. Further preferable are ethanol, propanol and butanol, and ethanol is particularly preferred as a work-up and production of noroxymorphone can be particularly simplified and carried out at lower temperature and cost.

With the total process of the present invention, including the new process step (iv) as well as process steps (i), (ii) and (iv), each individually improving the process, it has been surprisingly found that all of these improvements together can lead to an overall yield of 60% or more which compares favorably to the reported 37% of U.S. Pat. No. 5,112,975.

In the present invention, improvements in step (iv) of reacting the compound of formula (Va) or (Vb), or the compound of formula (V), respectively, to the compound of formula (VIa) or (VIb), or the compound of formula (VI), respectively; and optionally step (i) of reacting morphine of formula (II) to the compound of formula (IIIa) or (IIIb), or the compound of formula (III), respectively; step (ii) of reacting the compound of formula (IIIa) or (IIIb), or the compound of formula (III), respectively, to the compound of formula (IVa) or (IVb), or the compound of formula (IV), respectively; and step (vi) of reacting the compound of formula (VIIa) or (VIIb), or the compound of formula (VII), respectively, to noroxymorphone of formula (I), respectively, can be achieved. Other general process conditions in each step (iv), and optionally step (i), step (ii) and step (vi), respectively, such as setting suitable amounts of reactants and solvents, process conditions like temperature, reaction time and pressure, and mode of addition of reactants, etc., can be suitably set by the skilled person based on his general knowledge from the state of the art, e.g. the state of the art exemplified above, i.e. FR 2 515 184, U.S. Pat. No. 5,112, 975 and Ninan A.; Sainsbury M. (1992). "An improved synthesis of noroxymorphone", Tetrahedron 48 (11): 6709.

The further step (iii) of reacting the compound of formula (IVa) or (IVb), or the compound of formula (IV), respectively, to the compound of formula (Va) or (Vb), or the compound of formula (V), respectively, and step (v) of reacting the compound of formula (VIa) or (VIb), or the compound of formula (VI), respectively, to the compound of formula (VIIa) or (VIIb), or the compound of formula (VII), respectively, can be suitably carried out by the skilled person based on his general knowledge in view of the state of the art, e.g. the state of the art exemplified above, i.e. FR 2 515 184, U.S. Pat. No. 5,112,975 and Ninan A.; Sainsbury M. (1992). "An improved synthesis of noroxymorphone", Tetrahedron 48 (11): 6709. Also the general steps (i), (ii) and (vi) which do not lead to the improvements provided herein, as well as the general step (iv) which does not offer the improvements provided herein, can be suitably carried out based on the above state of the art and the general knowledge of the skilled person.

The present invention will now be described in more detail with reference to specific Examples. While the invention is described with reference to certain specific Examples thereof, it is clear to the skilled person that the invention is not limited to these specific Examples.

EXAMPLES

The analytical method used for purity and assay determination and reaction control is as follows:
High performance liquid chromatography (HPLC): Gemini C6-Phenyl ® column, 20 mM phosphate buffer (pH 7.72)/acetonitrile as liquid phase, 220 nm as UV detection wavelength.

Example 1

3-O,N-bis-ethoxycarbonyl-normorphine (compound III with $R^1$=ethoxycarbonyl (respectively $R^3$=ethyl))

Morphine (3.0 g) and potassium hydrogen carbonate (15 g) are suspended in dichloromethane (100 mL) at room temperature, i.e. about 20 to 25° C. Ethyl chloroformiate (7.8 mL) is added and the resulting mixture is refluxed until the reaction is complete (typically 6 hours). The reaction is quenched by addition of water. The organic phase, holding 98% of the desired product as proved by high-performance liquid chromatography (HPLC), is separated, washed with two additional portions of water and dried with sodium sulfate. The solvent is chased by vacuum distillation (40° C., <100 mbar) and the remainder is crystallized form a mixture of ethyl acetate and heptane yielding 4 g of the title compound (92% of theory).

Example 2

3-O,N-bis-ethoxycarbonyl-normorphinone (compound IV with $R^1$=ethoxycarbonyl (respectively $R^3$=ethyl))

Dimethylsulfoxide (2.5 g) is dissolved in dichloromethane (18 mL). At −80° C. oxalyl chloride (2 g) in dichloromethane (7 mL) followed by 3-O,N-bis-ethoxycarbonyl-morphine (4.5 g) in dichloromethane 8 mL) are added via the cold (−80° C.) reactor wall. The mixture is aged for two hours. Then triethylamine (4 g) is added via the cold reactor wall followed by gradual temperature increase to room temperature. The reaction is extracted several times with water and the solvent is chased by vacuum leaving 4.4 g of the title compound (98% of theory) with 97% HPLC purity.

Example 3

3-O,N-bis-ethoxycarbonyl-normorphinone dienol acetate (compound V with $R^1$=ethoxycarbonyl (respectively $R^3$=ethyl) and $R^2$=acetyl)

Sodium acetate (0.4 g) and 3-O,N-bis-ethoxycarbonyl-normorphinone (2.0 g) are aged at 90° C. in acetic acid anhydride (9 mL) until complete conversion (HPLC analysis; typical duration 5.5 h). Excess acetic acid anhydride is quenched with water and the main part of the solvent is removed by vacuum leaving a liquid residue of 6 g containing 2.3 g (97% of the theoretical value as analyzed by HPLC) of the title compound.

Example 4

3-O,N-bis-ethoxycarbonyl-14-hydroxynormorphinone (compound VI with $R^1$=ethoxycarbonyl (respectively $R^3$=ethyl))

A solution of 3-O,N-bis-ethoxycarbonyl-normorphinone dienol acetate in acetic acid (4.8 g assay of 3-O,N-bis-ethoxycarbonyl-normorphinone dienol acetate) is complemented with formic acid (until 33 g of acids are present) and water (4.5 g) at room temperature. To this solution a mixture of formic acid (9 g) and 30% hydrogen peroxide (1.45 g) which has been allowed to react for an induction time of 10 minutes is dosed at 0° C. within 1.5 hours. The mixture of formic acid and hydrogen peroxide is best formed at room temperature in a static mixer by continuous flow dosing of the two components using a residence time of 10 minutes. After aging the mixture at 0° C. for 2-3 hours it is directly used in Example 5. Optionally the reaction mixture is worked up: The reaction is then neutralized with aqueous sodium hydrogen carbonate and extracted into dichloromethane (400 mL) yielding 4.3 g of the title compound.

Comparative Example 1

3-O,N-bis-ethoxycarbonyl-14-hydroxynormorphinone (compound VI with $R^1$=ethoxycarbonyl (respectively $R^3$=ethyl))

A solution of 3-O,N-bis-ethoxycarbonyl-normorphinone dienol acetate (1.0 g) in formic acid (4.5 g) and water (0.5 g) is prepared at room temperature. 0.3 g of hydrogen peroxide (30%) is dosed at room temperature within 2 hours. After aging the mixture for 3 hours at room temperature (20-25° C.) it is worked up. The reaction is neutralized with aqueous sodium hydrogen carbonate and extracted into dichloromethane (80 mL) yielding 0.18 g of the title compound.

Example 5

3-O,N-bis-ethoxycarbonyl noroxymorphone (compound VII with $R^1$=ethoxycarbonyl (respectively $R^3$=ethyl))

The reaction mixture of example 4 is dosed onto a mixture of 2-propanol (10 mL) and palladium on charcoal (0.045 g) under hydrogen atmosphere (10 bar) as described in EP 2 377 866. After hydrogenation at room temperature overnight, the gas phase is exchanged for nitrogen and the catalyst is filtered off. The solvents are chased partly by vacuum and the remainder is analyzed for content of the title compound showing by HPLC a yield over example 4 & 5 of 88% of theory.

Example 6

Noroxymorphone (Compound I)

The remainder of example 5 is supplemented with 6 M sulfuric acid (24 mL) and ethanol (24 mL). The reaction mixture is refluxed until HPLC indicates total (>99%) consumption of the starting material and the intermediate (N-ethoxycarbonyl noroxymorphone) which takes typically 1 day. The reaction mixture is cooled and neutralized with ammonia to pH 9. The solids are isolated by suction filtration and are dried, yielding 2.2 g of the title compound (73% of theory based on the 3-O,N-bis-ethoxycarbonyl-normorphinone dienol acetate input) with 94% HPLC purity.

Example 7

3-O,N-bis-ethoxycarbonyl noroxymorphone (compound VII with $R^1$=ethoxycarbonyl (respectively $R^3$=ethyl))

Isolated 3-O,N-bis-ethoxycarbonyl-14-hydroxynormorphinone (4.7 g) is dissolved in 2-propanol (100 mL). Hydrogenation is performed using palladium on charcoal (0.25 g) at room temperature overnight at 3 bar hydrogen pressure. The catalyst is filtered off and the solvent is removed leaving 4.7 g of the title compound with 93% purity.

Example 8

Oxidation of 3-O,N-bis-ethoxycarbonyl-normorphine (compound III with $R^1$=ethoxycarbonyl (respectively $R^3$=ethyl)) without pre cooling of the solutions (Swern oxidation)

Dimethylsulfoxide (17 g) is dissolved in dichloromethane (115 mL). At −80° C. oxalyl chloride (14 g) in dichloromethane (40 mL) followed by 3-O,N-bis-ethoxycarbonyl-morphine (30 g) in dichloromethane 60 mL) are added directly into the reaction solution. The mixture is aged for two hours. Then triethylamine (27 g) is added followed by gradual temperature increase to room temperature. The reaction is extracted several times with water and the solvent is chased by vacuum leaving 28 g of a mixture of compound III (85%) and compound VIII (13%) with ($R^1$=ethyl for both products). Liquid chromatography-mass spectrometry (LC MS: ESI positive mode, Gemini C6-Phenyl ® column, 10 mM ammonium buffer (pH 8.5)/acetonitrile as liquid phase) analysis of the product proves the structure of compound VIII.

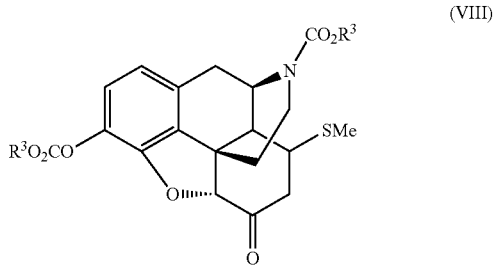

Example 9

3-O,N-bis-ethoxycarbonyl-14-hydroxynormorphinone (compound VI with $R^1$=ethoxycarbonyl (respectively $R^3$=ethyl))

A first solution of 3-O,N-bis-ethoxycarbonyl-normorphinone dienol acetate (1.0 g) in formic acid (2.5 g) and water (0.5 g) is prepared at room temperature. A second solution of 0.3 g of hydrogen peroxide (30%) in formic acid (2.0 g) is stirred for 10 minutes and then added to the first solution at room temperature within 2 hours. After aging the mixture for 3 hours at room temperature (20-25° C.) it is worked up. The reaction is neutralized with aqueous sodium hydrogen carbonate and extracted into dichloromethane (80 mL) yielding 0.33 g of the title compound.

The invention claimed is:

1. A process for producing noroxymorphone from morphine, comprising reacting morphine of formula (II)

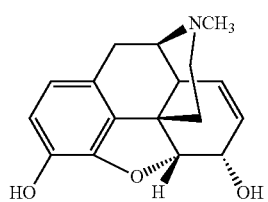
(II)

to a compound of formula (IIIa) or (IIIb),

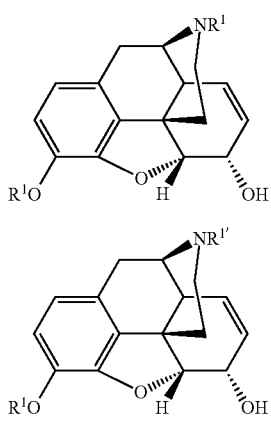
(IIIa)
(IIIb)

wherein
R$^1$ and R$^{1'}$ independently are a substituted or unsubstituted alkyl group with 1 to 20 carbon atoms or a substituted or unsubstituted aryl group, or a substituted or unsubstituted alkenyl group having 2 to 20 carbon atoms, or a substituted or unsubstituted carbonyloxyalkyl group with 1 to 20 carbon atoms in the alkyl residue, or a substituted or unsubstituted carbonyloxyaryl group or a substituted or unsubstituted carbonyloxyalkylaryl group with 1 to 20 carbon atoms in the alkyl residue, or a silyl group of formula Si(R$^4$)$_3$,
R$^4$ are the same or different and are each a substituted or unsubstituted alkyl group having 1 to 6 carbon atoms or an unsubstituted or substituted phenyl group;
reacting the compound of formula (IIIa) or (IIIb) to a compound of formula (IVa) or (IVb), respectively,

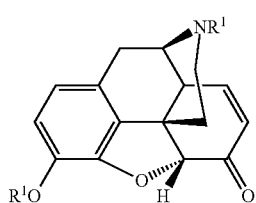
(IVa)

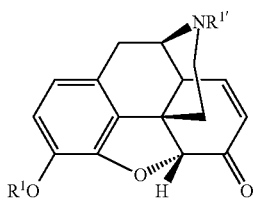
(IVb)

wherein
R$^1$ and R$^{1'}$ are defined as for the compound of formula (IIIa) and (IIIb),
wherein the reaction of the compound of formula (IIIa) or (IIIb) to a compound of formula (IVa) or (IVb), is conducted by a Swern oxidation with pre-cooling;
reacting the compound of formula (IVa) or (IVb) to a compound of formula (Va) or (Vb), respectively,

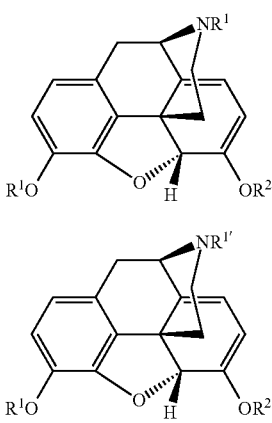
(Va)
(Vb)

wherein
R$^1$ and R$^{1'}$ independently are a substituted or unsubstituted alkyl group with 1 to 20 carbon atoms or a substituted or unsubstituted aryl group, or a substituted or unsubstituted alkenyl group having 2 to 20 carbon atoms, or a substituted or unsubstituted carbonyloxyalkyl group with 1 to 20 carbon atoms in the alkyl residue, or a substituted or unsubstituted carbonyloxyaryl group or a substituted or unsubstituted carbonyloxyalkylaryl group with 1 to 20 carbon atoms in the alkyl residue, or a silyl group of formula Si(R$^4$)$_3$,
R$^4$ are the same or different and are each a substituted or unsubstituted alkyl group having 1 to 6 carbon atoms or an unsubstituted or substituted phenyl group,
R$^2$ is a substituted or unsubstituted aliphatic or aromatic acyl group with 1 to 20 carbon atoms;
reacting the compound of formula (Va) or (Vb) to a compound of formula (VIa) or (VIb), respectively,

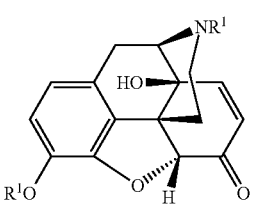
(VIa)

-continued (VIb)

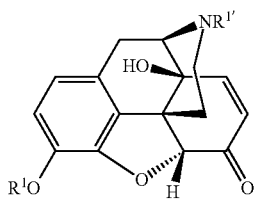

wherein
R¹ and R¹' are defined as for the compound of formula (Va) and (Vb),
wherein the reaction of the compound of formula (Va) or (Vb) to the compound of formula (VIa) or (VIb) is carried out with hydrogen peroxide and an organic acid, wherein the organic acid and the hydrogen peroxide are mixed and allowed to react for an induction time prior to addition to the compound of formula (Va) or (Vb);
reacting the compound of formula (VIa) or (VIb) to a compound of formula (VIIa) or (VIIb), respectively, (VIIa)

(VIIb)

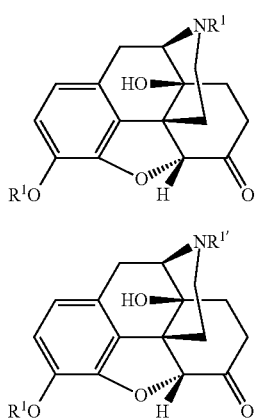

wherein
R¹ and R¹' are defined as for the compound of formula (VIa) and (VIb); and
reacting the compound of formula (VIIa) or (VIIb) to noroxymorphone of formula (I), (I)

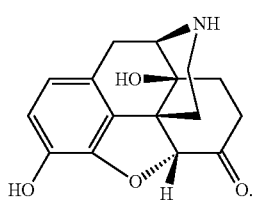

2. The process for producing noroxymorphone according to claim 1, wherein the mixing and reacting of the hydrogen peroxide and the organic acid is carried out in a separate vessel.

3. The process for producing noroxymorphone according to claim 1, wherein the mixing and reacting of the hydrogen peroxide and the organic acid is carried out by dosing two flows via a mixer, optionally in a continuous flow device.

4. The process for producing noroxymorphone according to claim 1, wherein the organic acid is formic acid or acetic acid.

5. The process for producing noroxymorphone according to claim 1, wherein the induction time is between 1 minute and 1 hour.

6. The process for producing noroxymorphone according to claim 1, wherein a part of the organic acid is added to the compound of formula (Va) or (Vb) prior to the addition of the mixture of hydrogen peroxide and the remaining organic acid.

7. The process for producing noroxymorphone according to claim 1, wherein the mixing and reacting of hydrogen peroxide and the organic acid is carried out at a temperature between −20° C. and 40° C.

8. The process for producing noroxymorphone according to claim 1, wherein the reacted mixture of hydrogen peroxide and the organic acid is added to the compound of formula (Va) or (Vb) over a time from 1 minute to 3 hours at a temperature between −40° C. and 40° C.

9. The process for producing noroxymorphone according to claim 1, wherein after the reaction of the compound of formula (Va) or (Vb) to the compound of formula (VIa) or (VIb) an aging step (iv-a) is carried out for 1 to 5 hours at a temperature between −40° C. and 40° C., and the obtained mixture is optionally worked up afterwards.

10. The process for producing noroxymorphone according to claim 1, wherein the reaction of morphine of formula (II) to a compound of formula (IIIa) or (IIIb) is carried out in absence of a toxic solvent.

11. The process for producing noroxymorphone according to claim 1, wherein the pre-cooling for the reaction of the compound of formula (IIIa) or (IIIb) to a compound of formula (IVa) or (IVb) is achieved by providing one or more pre-cooled solutions cooled to a temperature between −100° C. and 0° C., and/or achieved by adding the one or more solutions either via a cold reactor wall that is cooled to a temperature between −100° C. and 0° C. or achieved via a separate cooling device, optionally cooled to a temperature between −90° C. and −20° C.

12. The process for producing noroxymorphone according to claim 1, wherein the reaction of the compound of formula (VIIa) or (VIIb) to noroxymorphone of formula (I) is carried out in the presence of an organic solvent.

13. The process for producing noroxymorphone according to claim 12, wherein the reaction of the compound of formula (VIIa) or (VIIb) to noroxymorphone of formula (I) is carried out with a mixture comprising an aqueous acid and an organic solvent miscible with the aqueous acid, or with a mixture comprising an aqueous organic acid.

14. The process for producing noroxymorphone according to claim 1, wherein the pre-cooling for the reaction of the compound of formula (IIIa) or (IIIb) to a compound of formula (IVa) or (IVb) is achieved by providing one or more pre-cooled solutions cooled to a temperature between −90° C. and −20° C.

15. The process for producing noroxymorphone according to claim 1, wherein the mixing and reacting of hydrogen peroxide and the organic acid is carried out at room temperature.

16. The process for producing noroxymorphone according to claim 1, wherein the reacted mixture of hydrogen peroxide and the organic acid is added to the compound of formula (Va) or (Vb) over a time from 1 minute to 3 hours at a temperature between −20° C. and 20° C.

17. The process for producing noroxymorphone according to claim 1, wherein the reacted mixture of hydrogen peroxide and the organic acid is added to the compound of formula (Va) or (Vb) over a time from 1 minute to 3 hours at a temperature of about 0° C.

18. The process for producing noroxymorphone according to claim 1, wherein after the reaction of the compound of formula (Va) or (Vb) to the compound of formula (VIa) or (VIb) an aging step (iv-a) is carried out for 1 to 5 hours at a temperature between −20° C. and 20° C., and the obtained mixture is optionally worked up afterwards.

19. The process for producing noroxymorphone according to claim 1, wherein after the reaction of the compound of formula (Va) or (Vb) to the compound of formula (VIa) or (VIb) an aging step (iv-a) is carried out for 1 to 5 hours at a temperature of about 0° C., and the obtained mixture is optionally worked up afterwards.

20. The process for producing noroxymorphone according to claim 12, wherein the reaction of the compound of formula (VIIa) or (VIIb) to noroxymorphone of formula (I) is carried out with a mixture comprising an aqueous acid and an organic solvent miscible with the aqueous acid, wherein the organic solvent miscible with the aqueous acid is selected from the group consisting of alcohols, ethers, polyethers, sulfones and sulfoxides, or with a mixture comprising an aqueous organic acid.

\* \* \* \* \*